(12) United States Patent
Koshika et al.

(10) Patent No.: US 9,820,639 B2
(45) Date of Patent: Nov. 21, 2017

(54) IMAGE PROCESSING APPARATUS FOR SCANNING ENDOSCOPE

(71) Applicant: OLYMPUS CORPORATION, Tokyo (JP)

(72) Inventors: Soichiro Koshika, Mitaka (JP); Kazuma Kaneko, Hachioji (JP); Masanori Sumiyoshi, Hachioji (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/075,447

(22) Filed: Mar. 21, 2016

(65) Prior Publication Data
US 2016/0198933 A1 Jul. 14, 2016

Related U.S. Application Data

(63) Continuation of application No. PCT/JP2014/076034, filed on Sep. 30, 2014.

(30) Foreign Application Priority Data

Mar. 28, 2014 (JP) ................................ 2014-069673

(51) Int. Cl.
*A61B 1/06* (2006.01)
*A61B 1/07* (2006.01)
(Continued)

(52) U.S. Cl.
CPC .............. *A61B 1/07* (2013.01); *A61B 1/0002* (2013.01); *A61B 1/00009* (2013.01);
(Continued)

(58) Field of Classification Search
CPC ... A61B 1/00172; A61B 1/07; A61B 1/00009; A61B 1/043; A61B 5/0075;
(Continued)

(56) References Cited

U.S. PATENT DOCUMENTS

2001/0026157 A1 10/2001 Heid
2008/0021303 A1 1/2008 Krueger
(Continued)

FOREIGN PATENT DOCUMENTS

EP 2 808 718 A1 12/2014
JP 2001-292980 A 10/2001
(Continued)

OTHER PUBLICATIONS

International Search Report dated Dec. 22, 2014 issued in International Application No. PCT/JP2014/076034.
Japanese Office Action dated Sep. 1, 2015 from related Japanese Patent Application No. 2015-533354.

*Primary Examiner* — Alexandra Newton
(74) *Attorney, Agent, or Firm* — Scully, Scott, Murphy & Presser, P.C.

(57) ABSTRACT

An image processing apparatus for scanning endoscope includes: a number-of-interpolations determination section that receives detection signals from a detector for sequentially sampling return light from a subject and determines a number of detection signals used in an interpolation process by an interpolation section based on distances between a coordinate position of a predetermined lattice point in pixel data of a raster scan system and sampling coordinate positions of the detection signals around the coordinate position of the predetermined lattice point; and the interpolation section that generates pixel data of the predetermined lattice point by using signals of the sampling coordinate positions, wherein a number of the signals is equal to the number of detection signals determined by the number-of-interpolations determination section near the sampling coordinate position corresponding to the coordinate position of the predetermined lattice point.

6 Claims, 10 Drawing Sheets

(51) Int. Cl.
*A61B 1/00* (2006.01)
*A61B 1/04* (2006.01)
*G02B 23/26* (2006.01)

(52) U.S. Cl.
CPC ............ *A61B 1/00172* (2013.01); *A61B 1/04* (2013.01); *A61B 1/042* (2013.01); *A61B 1/0669* (2013.01); *G02B 23/26* (2013.01)

(58) Field of Classification Search
CPC ... A61B 5/0071; A61B 5/0068; A61B 1/0008; A61B 1/00165; G02B 21/008; G02B 26/103
See application file for complete search history.

(56) References Cited

U.S. PATENT DOCUMENTS

| | | |
|---|---|---|
| 2012/0241620 A1 | 9/2012 | On |
| 2012/0242859 A1 | 9/2012 | Sasaki |
| 2014/0332677 A1 | 11/2014 | Fujiwara et al. |

FOREIGN PATENT DOCUMENTS

| | | |
|---|---|---|
| JP | 2010-279434 A | 12/2010 |
| JP | 2011-125404 A | 6/2011 |
| JP | 2011-127933 A | 6/2011 |
| JP | 2013-121455 A | 6/2013 |
| WO | 2011/074447 A1 | 6/2011 |
| WO | 2011/074448 A1 | 6/2011 |
| WO | 2013/111604 A1 | 8/2013 |

Rd

IMAGE PROCESSING APPARATUS FOR SCANNING ENDOSCOPE

CROSS REFERENCE TO RELATED APPLICATION

This application is a continuation application of PCT/JP2014/076034 filed on Sep. 30, 2014 and claims benefit of Japanese Application No. 2014-069673 filed in Japan on Mar. 28, 2014, the entire contents of which are incorporated herein by this reference.

BACKGROUND OF THE INVENTION

1. Field of the Invention

The present invention relates to an image processing apparatus for a scanning endoscope that scans a subject with light to acquire an image.

2. Description of the Related Art

In recent years, endoscopes have been widely used in a medical field and the like. Various techniques for reducing a diameter of an insertion portion inserted to a subject are also proposed. An example of the techniques includes a scanning endoscope apparatus.

A conventional example of the scanning endoscope apparatus disclosed in Japanese Patent Application Laid-Open Publication No. 2013-121455 includes: an optical fiber that guides illuminating light to an emission end to emit the illuminating light to an object; optical fiber scanning means for periodically moving the emission end of the optical fiber for periodical scanning with the illuminating light emitted from the emission end of the optical fiber in a two-dimensional scanning region on the object; light source control means for generating a drive signal for driving the illuminating light to control ON/OFF of the illuminating light based on the drive signal; image signal detection means for receiving scattered light from the object to detect image signals at predetermined detection timing; and image generation means for allocating two-dimensional pixel positions according to the detection timing of the image signals and arranging the image signals on the pixel positions to generate an endoscopic image, wherein the light source control means generates the drive signal based on the detection timing of the image signals to make irradiation density of the illuminating light substantially constant in an entire area of the scanning region.

The conventional example also discloses that in conversion of a pixel (detection signal) detected by scanning in a spiral shape with the illuminating light emitted from the emission end of the optical fiber into a pixel of a raster scan system, pulsed light is emitted (and turned off) such that only one detection signal exists when a plurality of detection signals exist in a subregion assumed to be the latter pixel.

SUMMARY OF THE INVENTION

An aspect of the present invention provides an image processing apparatus for scanning endoscope including: a number-of-interpolations determination section that receives detection signals from a detection section for sequentially sampling return light from a subject scanned with illuminating light by a scanning endoscope and determines a number of detection signals used in an interpolation process by an interpolation section based on information of a coordinate position of a predetermined lattice point in pixel data of a raster scan system and sampling coordinate positions of the detection signals around the coordinate position of the predetermined lattice point; and the interpolation section that generates pixel data of the predetermined lattice point by using signals of the sampling coordinate positions, wherein a number of the signals is equal to the number of detection signals determined by the number-of-interpolations determination section near the sampling coordinate position of the detection signal corresponding to the coordinate position of the predetermined lattice point.

DETAILED DESCRIPTION OF THE PREFERRED EMBODIMENT

Hereinafter, an embodiment of the present invention will be described with reference to the drawings.

First Embodiment

Figure 1:
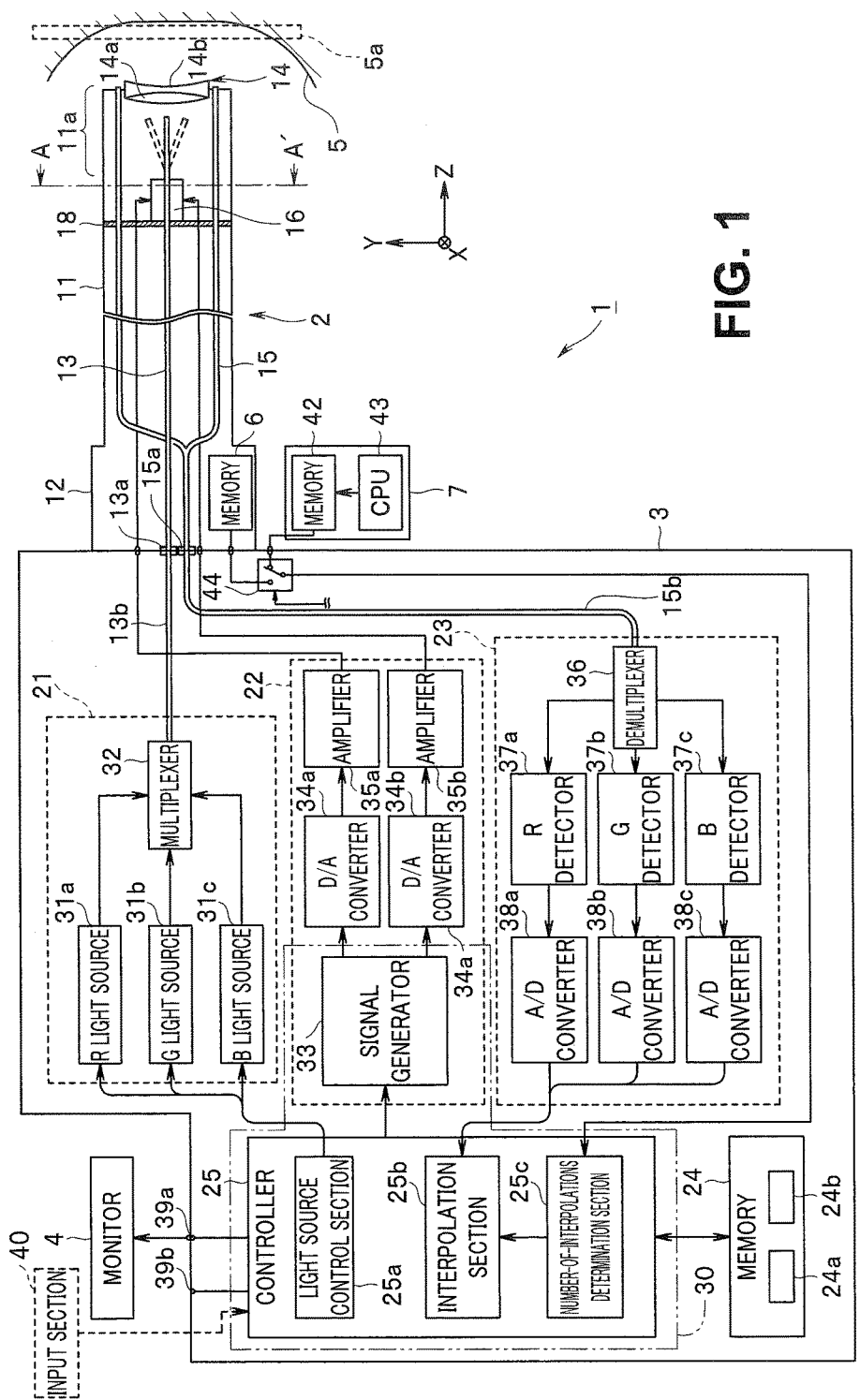
FIG. 1 is a diagram showing an entire configuration of a scanning endoscope apparatus according to a first embodiment of the present invention.

As shown in FIG. 1, a scanning endoscope apparatus 1 of a first embodiment of the present invention includes: a scanning endoscope 2 inserted to a body cavity of a subject 5; a main body apparatus (or a scanning endoscope control apparatus) 3 in which the scanning endoscope 2 is detachably connected; and a monitor 4 as a display apparatus connected to the main body apparatus 3. In the present embodiment, the scanning endoscope apparatus 1 includes, for example, a personal computer (abbreviated as PC) 7 that applies an adjustment process to a memory 6 provided in the scanning endoscope 2 and forming a saving section that two-dimensionally saves coordinate position information, wherein the adjustment process is for reducing the coordinate position information and storing the coordinate position information in the memory 6. Note that the PC 7 is not necessary after the coordinate position information is stored in the memory 6.

The scanning endoscope 2 includes an insertion portion 11 formed in an elongated shape and with flexibility, and the insertion portion 11 can be inserted to a body or a body cavity of the subject 5. A connector 12 for detachably connecting the scanning endoscope 2 to the main body apparatus 3 is provided on a proximal end portion of the insertion portion 11.

An illumination optical fiber 13 that serves as a light guide member for guiding illuminating light supplied from a light source unit 21 of the main body apparatus 3 is inserted to the insertion portion 11, from the proximal end portion to near a distal end portion 11a. The guided illuminating light is emitted from a distal end of the illumination optical fiber 13 toward an object, such as an inspected site in the subject 5, through an opposing condensing optical system 14.

A light receiving optical fiber 15 for receiving return light from the subject 5 (object on the side of the subject 5) to guide the return light to a detection unit 23 that forms a detection section of the main body apparatus 3 is also inserted to the insertion portion 11.

An end portion including a light incident surface of the illumination optical fiber 13 is connected through an optical connector 13a to an end portion on a distal end side of an illumination optical fiber 13b provided inside of the main body apparatus 3, and an end portion including a light incident surface on a proximal end side of the illumination optical fiber 13b is arranged on a multiplexer 32 in the light source unit 21.

An end portion including a light emission surface of the illumination optical fiber 13 is arranged in a state that an actuator section (or actuators) 16 can move the end portion, in a state that the end portion is close to and opposite to the condensing optical system 14 provided on the distal end portion 11a of the insertion portion 11.

An end portion including a light incident surface of the light receiving optical fiber 15 is arranged, for example, along a circular shape around a light emission surface of the condensing optical system 14, on a distal end surface of the distal end portion 11a of the insertion portion 11. An end portion on the proximal end side that is a light emission surface of the light receiving optical fiber 15 is connected through an optical connector 15a to an end portion on the distal end side of a light receiving optical fiber 15b provided inside of the main body apparatus 3, and an end portion on the proximal end side of the light receiving optical fiber 15b is arranged on a demultiplexer 36 in the detection unit 23.

The condensing optical system 14 forms an optical system with an achromatic function including a convex lens 14a and a concave lens 14b and condenses illuminating light from a distal end surface of the illumination optical fiber 13 to emit the light to an object side.

The actuator section 16 that forms a drive section (or a drive device) for driving the distal end side of the illumination optical fiber 13 in a direction orthogonal to a longitudinal direction of the illumination optical fiber 13 based on a drive signal outputted from a drive unit 22 of the main body apparatus 3 is provided on an intermediate part of the illumination optical fiber 13, near the distal end portion 11a in the insertion portion 11.

As described below, the actuator section 16 expands or contracts in a Z axis direction as a result of application of a drive signal, wherein the Z axis direction is a longitudinal direction of the illumination optical fiber 13. In this way, the actuator section 16 moves on the distal end side of the illumination optical fiber 13 as indicated by a dotted line, from a state indicated by a solid line in FIG. 1. With the illuminating light emitted from the distal end surface of the illumination optical fiber 13, the actuator section 16 performs scanning in X and Y axis directions perpendicular to the Z axis.

A support member 18 fixes a proximal end side part of the actuator section 16 in the Z axis direction of the actuator section 16 to an inner surface of the insertion portion 11 to facilitate scanning in the X and Y axis directions with the distal end side of the illumination optical fiber 13 when the actuator section 16 is driven by the application of the drive signal.

Figure 2:
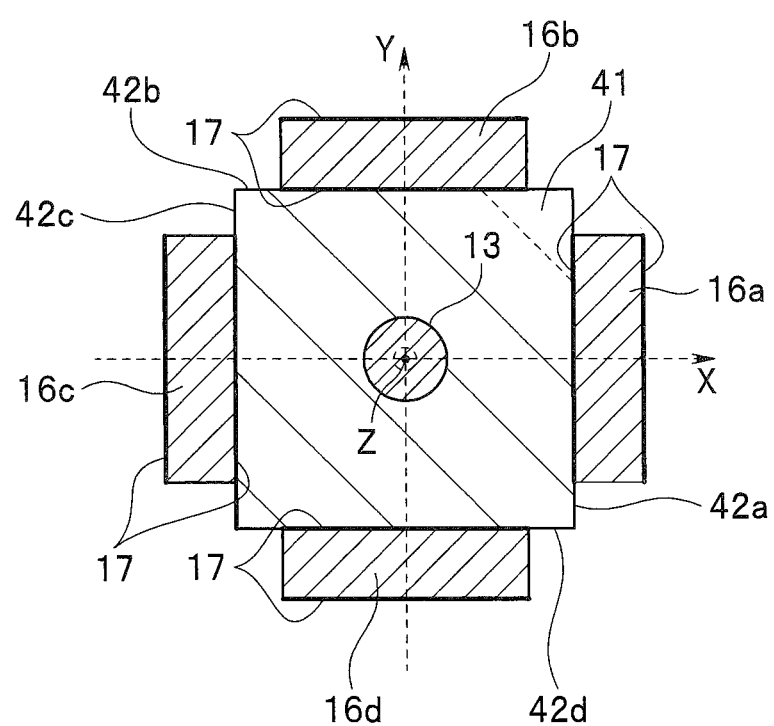
FIG. 2 is a cross-sectional view showing a configuration of actuators that form a drive section.

The illumination optical fiber 13 and the actuator section 16 are respectively arranged to have a positional relationship as shown for example in FIG. 2, in a cross section perpendicular to the longitudinal axis direction of the insertion portion 11. FIG. 2 is a cross-sectional view showing a configuration of the actuator section 16 provided in the scanning endoscope 2.

As shown in FIG. 2, a ferrule 41 as a joint member is arranged between the illumination optical fiber 13 and the actuator section 16. More specifically, the ferrule 41 is formed by, for example, zirconia (ceramic) or nickel.

As shown in FIG. 2, the ferrule 41 is formed to have a quadrangular prism and includes: side surfaces 42a and 42c perpendicular to the X axis direction (left-right direction in the drawing); and side surfaces 42b and 42d perpendicular to the Y axis direction (up-down direction in the drawing). The illumination optical fiber 13 is fixed to a center of the ferrule 41.

As shown in FIG. 2, the actuator section 16 includes an actuator 16a arranged along the side surface 42a, an actuator 16b arranged along the side surface 42b, an actuator 16c arranged along the side surface 42c, and an actuator 16d arranged along the side surface 42d.

In other words, the actuator section 16 with a function as a drive section for optical scanning includes a pair of actuators 16a and 16c opposing the Y axis and a pair of actuators 16b and 16d opposing the X axis, across the illumination optical fiber 13.

Each of the actuators 16a, 16b, 16c, and 16d drives the illumination optical fiber 13 according to the drive signals outputted from the drive unit 22 arranged in the main body apparatus 3.

A polarization process is applied to the actuators 16a to 16d such that polarization directions become predetermined directions, respectively, and the actuators 16a to 16d are formed by piezoelectric devices provided with electrodes 17 on opposing sides.

For example, the actuator 16a is formed by a piezoelectric device applied in advance with the polarization process such that the polarization direction coincides with a negative direction (direction from right to left in FIG. 2) of the X axis.

The actuator 16a is configured to contract in the Z axis direction (normal direction in the drawing) when a voltage with a positive value is applied according to the drive signal outputted from the drive unit 22 (when a direction of an electric field generated along with the supply of the drive signal is a forward direction relative to the polarization direction) and to expand in the Z axis direction when a voltage with a negative value is applied (when the direction of the electric field generated along with the supply of the drive signal is an opposite direction relative to the polarization direction).

The opposing actuators 16a and 16c and the opposing actuators 16b and 16d are set to expand and contract in opposite directions according to the drive signals outputted from the drive unit 22, respectively. Alternatively, each of the opposing actuators 16a and 16c and the opposing actuators 16b and 16d may have same characteristics, and phases when the drive signals are applied may be opposite (more specifically, the connections of two signal lines for applying the drive signals to the pairs of electrodes 17 can be opposite in the opposing actuators 16a and 16c and the opposing actuators 16b and 16d).

Note that four actuators 16a to 16d may not be used when piezoelectric devices with a high function of expansion and contraction are used or when large scanning is not necessary, and for example, two orthogonal actuators 16a and 16b may form the actuator section 16. In the following description, a case of two orthogonal actuators 16a (and 16c) and 16b (and 16d) will be described.

Figure 3A:
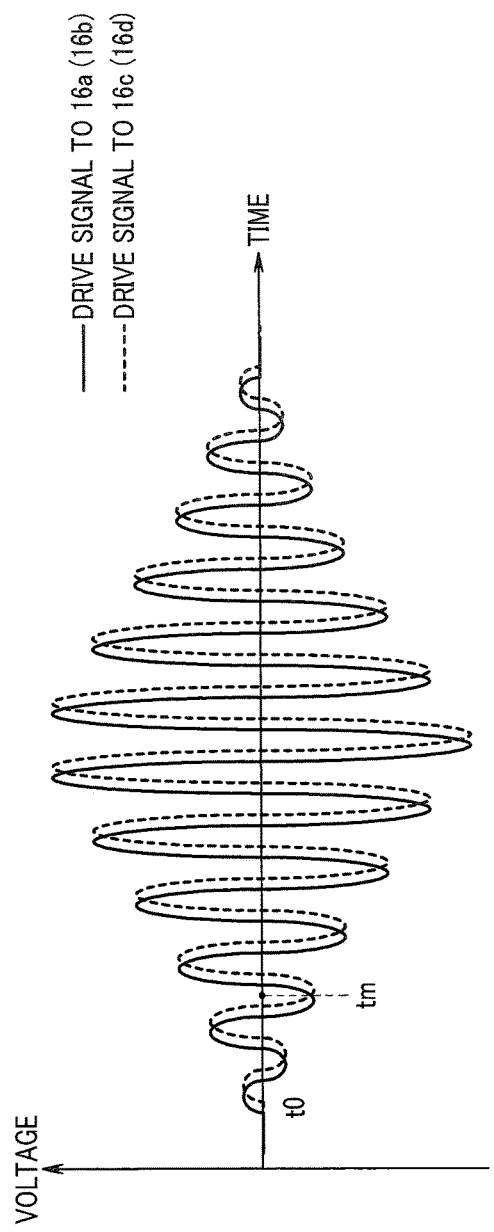
FIG. 3A is a diagram showing waveforms of drive signals for driving the actuators.

FIG. 3A shows waveforms of the drive signals for driving the actuator 16a (and 16c) (same in the case of 16b (and 16d)).

As shown in FIG. 3A, the drive signals for driving the actuator 16a (and 16c) and the actuator 16b (and 16d) have substantially the same waveforms in which a phase of one of the drive signals is shifted, and the waveforms are changed in a sine wave shape. The voltage is gradually increased from a value of 0 equivalent to a scan start position Pst (see FIG. 3B) to a value equivalent to a scan end position Pen (see FIG. 3B), and then the voltage is gradually reduced again to return the voltage to the value of 0 equivalent to the scan start position Pst.

Figure 3B:
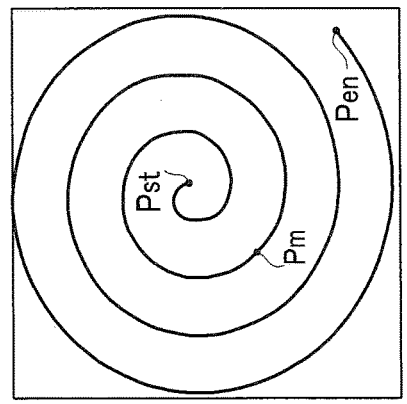
FIG. 3B is a diagram showing a trajectory of swinging of a distal end of an optical fiber based on the drive signals of FIG. 3A.

The drive signals are applied to the actuator 16a (and 16c) and the actuator 16b (and 16d), and the distal end side of the illumination optical fiber 13 driven by the actuator section 16 is moved (scanned) in a spiral shape from the scan start position Pst to the scan end position Pen as shown in FIG. 3B. Note that information for generating the drive signals with the drive waveforms as shown in FIG. 3A is stored in, for example, a drive information storage area 24a in a memory 24. A controller 25 in the main body apparatus 3 refers to the information in the drive information storage area 24a, and a drive unit 22 generates the drive signals with the drive waveforms as shown in FIG. 3A to drive the actuator section 16. Note that the information for generating the drive signals with the drive waveforms may be stored in a saving medium or the like other than the memory 24. For example, a memory or the like for storing the information may be provided inside of the controller 25.

Information of frequencies and signal amplification factors of the drive signals is stored as the information for generating the drive signals in the memory 24. The frequency of the drive signal is a resonance frequency when the distal end of the optical fiber oscillates or a frequency near the resonance frequency. The signal amplification factor is information necessary for obtaining a scanning trajectory of spirals in a desired size. Note that the signal amplification factor may be set in advance based on the resonance frequency of the distal end of the optical fiber. Information of the signal amplification factor set in association with the resonance frequency of the distal end of the optical fiber may be stored in a saving medium such as the memory 24.

As shown in FIG. 1, the memory 6 forming a saving section (or a saving device) that saves (stores) individual identification information of the scanning endoscope 2 and information of two-dimensional coordinate positions of the illumination optical fiber 13 when the distal end side of the illumination optical fiber 13 is driven to discretely emit pulsed light is provided inside of the scanning endoscope 2, such as inside of the connector 12 of the proximal end portion of the insertion portion 11.

In the present embodiment, the information of the two-dimensional coordinate positions of the illumination optical fiber 13 when the distal end side of the illumination optical fiber 13 is driven to discretely emit pulsed light is saved (stored) in advance in a memory 42 in the PC 7, and the information of the coordinate positions is used to execute a conversion process (or an interpolation process) including interpolation for converting the detection signals received by the light receiving optical fiber 15 into pixel data of a raster scan system. After the end of the interpolation process, only the information of the coordinate positions used in the interpolation process is saved in the memory 6. In this way, a memory capacity of the memory 6 can be reduced. The PC 7 includes the memory 42 and a central processing unit (abbreviated as CPU) 43 that controls the PC 7 including the memory 42.

In other words, assuming that the memory 6 is a second saving section, information of a larger number of coordinate positions exceeding the information of the number of coordinate positions ultimately necessary in the interpolation process is saved in advance in a first saving section formed by the memory 42 and the like. As a result of the interpolation process, only the information of the number of coordinate positions actually used in the interpolation process is extracted (from the information of the number of coordinate positions before the interpolation process) and stored in the memory 6 included in the scanning endoscope 2 including the illumination optical fiber 13, the actuator section 16, the condensing optical system 14, and the like at the actual interpolation process.

In this way, after the interpolation process, only the position information saved (stored) in the second saving section is the position information necessary in subsequent endoscopy in the scanning endoscope 2 including the second saving section. Note that a section including the first saving section and the second saving section can also be defined as the saving section.

The information of the coordinate positions stored in the memory 42 in the PC 7 is read by the controller 25 of the main body apparatus 3 through, for example, a selector switch 44 provided in the main body apparatus 3 and is stored in, for example, the memory 24. Therefore, the memory 42 in the main body apparatus 3 can be assumed to form the first saving section in the saving section. Note that switching of a contact point of the selector switch 44 is performed by, for example, the controller 25.

The main body apparatus 3 includes: the light source unit 21 forming light source(s) that generates (or creates) illuminating light to supply the generated illuminating light to the proximal end side of the illumination optical fiber 13 of the scanning endoscope 2; the drive unit 22 that generates drive signals for two-dimensional scan with the distal end of the illumination optical fiber 13; the detection unit 23 that detects return light by using the light receiving optical fiber 15 for receiving the return light of the illuminating light emitted from the distal end of the illumination optical fiber 13; the memory 24 that temporarily saves data used for the interpolation (or the interpolation process) and that is used as a work area; and the controller 25 that controls the entire main body apparatus 3. Note that the interpolation and the interpolation process have the same meaning in the present description.

The light source unit 21 includes: an R light source 31a that generates light in a wavelength band of red (also called R light); a G light source 31b that generates light in a wavelength band of green (also called G light); a B light source 31c that generates light in a wavelength band of blue (also called B light); and the multiplexer 32.

The R light source 31a, the G light source 31b, and the B light source 31c are formed by using, for example, laser light sources and emit the R light, the G light, and the B light to the multiplexer 32, respectively, when the R light source 31a, the G light source 31b, and the B light source 31c are turned on by the control by the controller 25. The controller 25 includes a light source control section 25a formed by a CPU or the like that controls discrete light emission of the R light source 31a, the G light source 31b, and the B light source 31c. When the actuator section 16 drives the illumination optical fiber 13, the light source control section 25a controls the light emission of the R light source 31a, the G light source 31b, and the B light source 31c to emit pulsed light at drive timing for the discrete coordinate positions saved in the memory 42.

Note that in the present embodiment, the controller 25 transmits control signals for simultaneous and pulsed light emission to the R light source 31a, the G light source 31b, and the B light source 31c, and the R light source 31a, the G light source 31b, and the B light source 31c simultaneously generate the R light, the G light, and the B light and emit the R light, the G light, and the B light to the multiplexer 32.

The multiplexer 32 multiplexes the R light from the R light source 31a, the G light from the G light source 31b, and the B light from the B light source 31c and supplies the light to the light incident surface of the illumination optical fiber 13b. The illumination optical fiber 13b supplies the multiplexed R light, G light, and B light toward the illumination optical fiber 13.

The drive unit 22 has a function as a drive signal output section (or a drive signal output unit) that outputs drive signals and includes a signal generator 33, D/A converters 34a and 34b, and amplifiers 35a and 35b.

The signal generator 33 generates drive signals for moving (or swinging) the end portion including the light emission surface of the illumination optical fiber 13 based on the control by the controller 25 and outputs the drive signals to the D/A converters 34a and 34b. Note that as indicated by an alternate long and two short dashes line in FIG. 1, the controller 25 and the signal generator 33 may be formed by a programmable semiconductor such as an FPGA (field programmable gate array) 30. The controller 25 and the signal generator 33 may also be formed by the FPGA 30 or the like in a scanning endoscope apparatus 1B of FIG. 10 described later.

The D/A converters 34a and 34b convert digital drive signals outputted from the signal generator 33 into analog drive signals and output the analog drive signals to the amplifiers 35a and 35b, respectively.

The amplifiers 35a and 35b amplify the drive signals outputted from the D/A converters 34a and 34b, respectively, and output the signals as the drive signals shown in FIG. 3A to the actuator section 16.

On the other hand, the detection unit 23 includes the demultiplexer 36, detectors 37a, 37b, and 37c, and A/D converters 38a, 38b, and 38c.

The demultiplexer 36 includes a dichroic mirror and the like and is configured to demultiplex the return light emitted from the light emission surface of the light receiving optical fiber 15 to light of each color component of R (red), G (green), and B (blue) and to emit the light to the detectors 37a, 37b, and 37c.

The detectors 37a, 37b, and 37c are formed by photodetectors, such as photodiodes, and detect an intensity of the R light, an intensity of the G light, and an intensity of the B light outputted from the demultiplexer 36, respectively. The detectors 37a, 37b, and 37c generate analog R, G, and B detection signals corresponding to the detected intensities of the R light, the G light, and the B light, respectively, and output the signals to the A/D converters 38a, 38b, and 38c.

The A/D converters 38a, 38b, and 38c convert the analog R, G, and B detection signals respectively outputted from the detectors 37a, 37b, and 37c into digital R, G, and B detection signals, respectively, and output the signals to the controller 25.

A control program and the like for controlling the main body apparatus 3 are stored in advance in the memory 24. The information of the coordinate positions read by the controller 25 of the main body apparatus 3 from the memory 42 is also stored in the memory 24.

The controller 25 is formed by using a CPU or the like and reads the control program stored in the memory 24 to control the light source unit 21 and the drive unit 22 based on the read control program.

That is, the actuator section 16 with a function as a drive section causes the illumination optical fiber 13 to swing such as to depict a trajectory according to a predetermined scanning pattern in which irradiation positions of illuminating light emitted to the object form a spiral shape, based on the drive signals outputted from the drive unit 22 according to the control by the controller 25.

The light source control section (or light source control circuit) 25a of the controller 25 controls the R light source 31a, the G light source 31b, and the B light source 31c to sequentially and discretely emit light at each coordinate position according to the information of the coordinate positions saved in advance in the memory 42. The detection unit 23 samples the R, G, and B detection signals to acquire the return light from the object at the timing of the light emission at each coordinate position and sets, as sampling coordinate positions, the coordinate positions saved in advance in the memory 42 as coordinate positions when the signals are acquired.

Note that when the light source control section 25a controls the R light source 31a, the G light source 31b, and the B light source 31c to sequentially and discretely emit light at the same time along the scanning pattern at each coordinate position saved in the memory 42, the light source control section 25a may cause the R light source 31a, the G light source 31b, and the B light source 31c to emit light according to information of time periods corresponding to each coordinate position saved in the memory 42.

That is, when the light source control section 25a moves the distal end of the illumination optical fiber 13 along the scanning pattern (scanning trajectory) in the spiral shape shown in FIG. 3B, the light source control section 25a performs the control for the sequential light emission at each coordinate position on the scanning pattern saved in the memory 42. However, in place of each coordinate position, the light source control section 25a may cause the R light source 31a, the G light source 31b, and the B light source 31c to emit light (emit pulsed light) at each time period of the drive signals shown in FIG. 3A equivalent to each coordinate position.

For example, a scan start time period corresponding to the scan start position Pst in FIG. 3B is set as t0 in FIG. 3A, and for example, the coordinate position for the light emission saved in the memory 42 is set as Pm (see FIG. 3B). In this case, the R light source 31a, the G light source 31b, and the B light source 31c may be controlled to simultaneously emit light (emit pulsed light) at a time period tm in FIG. 3A corresponding to Pm.

Therefore, for example, the light source control section 25a may have a function of a coordinate position/time period conversion section (or a coordinate position/time period conversion circuit) that converts the information of the coordinate positions for the light emission of the light sources saved in the memory 42 (the memory 6) into the information of the time periods along the drive waveforms of the drive signals. The light source control section 25a may cause the R light source 31a, the G light source 31b, and the B light source 31c as the light sources to emit light at the time periods corresponding to the coordinate positions for the light emission of the light sources on the scanning pattern, when the drive waveforms of the drive signals are changed with a lapse of the time period as shown in FIG. 3A according to the case in which the distal end of the illumination optical fiber 13 is driven to move along the scanning pattern (scanning trajectory) in the spiral shape as shown in FIG. 3B.

The controller 25 generates an image corresponding to each coordinate position in the scanning pattern in the spiral shape based on the R, G, and B detection signals outputted from the detection unit 23.

Figure 4A:
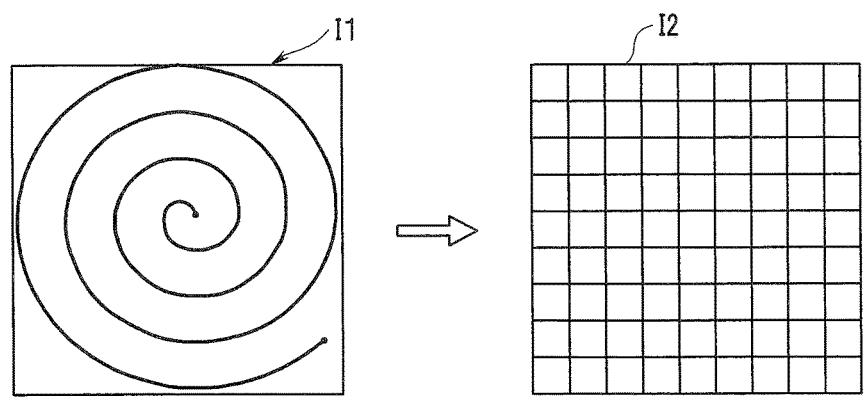
FIG. 4A is an explanatory diagram for conversion into a raster scan image from a trajectory of laser light emitted from the distal end of the optical fiber and from detection signals obtained by receiving the laser light.

The controller 25 also includes an interpolation section (or interpolation circuit) 25b including a central processing unit (abbreviated as CPU) or the like that performs interpolation to convert an image I1 corresponding to the predetermined scanning pattern in the spiral shape as shown on a left side of FIG. 4A into an image 12 of the raster scan system in which pixel data is arranged on each square lattice point as shown on a right side of FIG. 4A. In other words, the controller 25 includes the interpolation section 25b that performs interpolation to convert the (R, G, and B) detection signals forming the image I1 corresponding to the predetermined scanning pattern in the spiral shape as shown on the left side of FIG. 4A into the pixel data of the raster scan system in which the pixel data is arranged on each square lattice point as shown on the right side of FIG. 4A. Each lattice point serves as the coordinate position of each pixel data of the raster scan system or the coordinate position of each pixel.

Figure 4B:
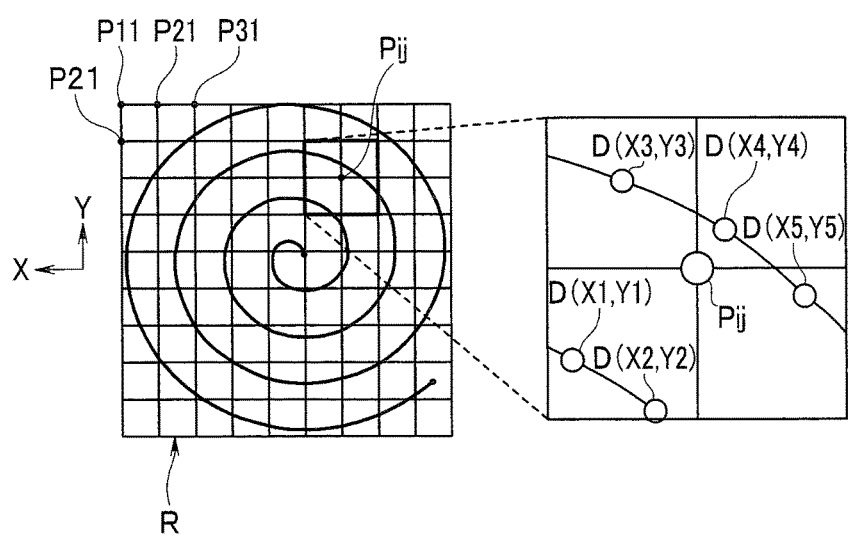
FIG. 4B is an explanatory diagram for performing the conversion of FIG. 4A.

For example, the interpolation section 25b executes an interpolation process as in an enlarged view on a right side of FIG. 4B in a state in which the coordinate position at the discrete light emission while the distal end of the illumination optical fiber 13 is moved along the predetermined scanning pattern in the spiral shape (the coordinate position is a sampling coordinate position sampled and acquired by the detection unit 23 forming the detection section) and the coordinate position of each lattice point provided with the pixel data of the raster scan system are arranged at the same time on one coordinate as shown on a left side of FIG. 4B.

The interpolation section 25b executes an interpolation process of using the detection signals as pixel data of the sampling coordinate positions existing around the coordinate position of a lattice point Pij to be interpolated to thereby generate pixel data of the lattice point Pij to be interpolated as shown in the enlarged view on the right side of FIG. 4B.

The enlarged view of FIG. 4B shows detection signals D (X1, Y1) to D (X5, Y5) of sampling coordinate positions (Xi, Yj) existing around the lattice point Pij. In the following description, notation of (Xi, Yj) of the sampling coordinate positions (Xi, Yj) is omitted, and the detection signals D will be mainly used for the description. The coordinate position of the lattice point Pij will be expressed by a coordinate position (i, j) with (X=i, Y=j), wherein a unit is a distance d between lattice points as described later.

The controller 25 also includes a number-of-interpolations determination section (or a number-of-interpolations determination circuit) 25c including a CPU or the like that specifies the sampling coordinate positions to be used in the interpolation process by the interpolation section 25b based on lattice point coordinate position information indicating the information of the coordinate position (i, j) of the lattice point Pij and sampling coordinate position information as information of the sampling coordinate positions of the detection signals around the coordinate position (i, j) of the lattice point Pij and that determines the number of detection signals D used in the interpolation process by the interpolation section 25b according to the specified sampling coordinate positions, when the interpolation section 25b executes the interpolation of converting the detection signals corresponding to the predetermined scanning pattern into the pixel data of the raster scan system. Although FIG. 1 illustrates a configuration in which the number-of-interpolations determination section 25c is provided outside of the interpolation section 25b, the interpolation section 25b may have a function of the number-of-interpolations determination section 25c.

In the present embodiment, when the number-of-interpolations determination section 25c determines the number of detection signals D to be used in the interpolation process, the number-of-interpolations determination section 25c determines the number of detection signals D according to information of a plurality of concentric circular regions A1, A2, and the like (described later) set according to distance ranges from each lattice point Pij.

For example, a region information storage area 24b in the memory 24 stores in advance information for determining or setting the plurality of concentric circular regions A1, A2, and the like set according to the distance ranges from each lattice point Pij. The region information storage area 24b in the memory 24 stores, for example, information of radii indicating sizes of circular shapes of the regions A1, A2, and the like.

Note that the information for determining or setting the plurality of regions A1, A2, and the like may be stored in a saving section, such as a saving medium, other than the memory 24. For example, a memory or the like that forms a region information storage section for storing the information for determining or setting the plurality of regions A1, A2, and the like may be provided in the interpolation section 25b or the number-of-interpolations determination section 25c. The number-of-interpolations determination section 25c also stores (saves) in advance information for determining the number of detection signals D used in the interpolation process according to each region in the plurality of concentric circular regions A1, A2, and the like set according to the distance ranges from each lattice point Pij.

The interpolation section 25b can generate pixel data of the raster scan system with good image quality by preferentially using the detection signals D existing in regions closer to each lattice point Pij in the interpolation process as described later.

In the present embodiment, pixel data of the raster scan system with good image quality can be generated by executing the interpolation process so as to generate pixel data of the raster scan system without missing pixel data, in the lattice points Pij included at least within a predetermined scan range.

In the present embodiment, the sampling coordinate positions of the detection signals used in the interpolation process are saved in, for example, the memory 24. After the determination of the detection signals D used in the interpolation process for generating the pixel data of the raster scan system by the number-of-interpolations determination section 25c, the controller 25 switches the contact point of the selector switch 44 from the state shown in FIG. 1 and saves, in the memory 6, only the information of the sampling coordinate positions of the detection signals D used in the interpolation process, for example. In this way, the memory 6 with a small memory capacity provided on the scanning endoscope 2 can be subsequently used for the endoscopy.

The image I2 of the raster scan system generated by the interpolation process by the interpolation section 25b in the controller 25 is outputted from an image output end 39a to the monitor 4, and the image I2 of the raster scan system is displayed as an endoscopic image on a display surface of the monitor 4.

In the present embodiment, the controller 25 includes a second image output end 39b to allow attaching the information of the sampling coordinate positions of the detection signals detected by the detection unit 23 to the detection signals and outputting the signals from the second image output end 39b. In a general image of the raster scan system, RAW data includes only listing of luminance information. Since two-dimensional positions when the detection signals D are acquired are uncertain in the luminance information including the color components detected by the detection unit 23 in the present embodiment, the information of the sampling coordinate positions of the detection signals D are attached to the detection signals D to output the signals, for example. A RAW image can be generated from the detection signals D and the information of the sampling coordinate positions attached to the detection signals D, and the detection signals D and the information can be used in image processing. Note that although the controller 25, the light source control section 25a, the interpolation section 25b, and the number-of-interpolations determination section 25c are formed by the CPU, the configuration is not limited to this, and dedicated hardware may be used to form the controller 25, the light source control section 25a, the interpolation section 25b, and the number-of-interpolations determination section 25c.

The scanning endoscope apparatus 1 of the present embodiment includes: the light source unit 21 as a light source that generates (creates) illuminating light to be emitted to the subject; the illumination optical fiber 13 as an optical fiber for guiding the illuminating light from the proximal end to the distal end; the actuator section 16 as a drive section that drives the distal end of the optical fiber from the scan start position Pst to the scan end position Pen so as to scan the subject with the illuminating light; the light source control section 25a that controls the light source (emission of the illuminating light by the light source) to discretely emit the illuminating light while the drive section drives the distal end of the optical fiber; the detection unit 23 as a detection section that acquires the detection signals D by sequentially sampling the return light from the subject illuminated by the discretely emitted illuminating light; the memory 6 (or the memories 6 and 24 or 6 and 42) as a saving section that saves, as the sampling coordinate position information of the detection signals D, the information equivalent to the two-dimensional coordinate positions where the drive section has driven the distal end of the optical fiber at the timing of sequential sampling and acquisition of the detection signals D by the detection section; the interpolation section 25b that performs the interpolation of converting the detection signals acquired by the detection section in the period in which the distal end of the optical fiber is driven from the scan start position Pst to the scan end position, into the pixel data of the raster scan system arranged at the coordinate positions of the lattice point; and the number-of-interpolations determination section 25c that specifies the sampling coordinate positions of the detection signals used in the interpolation process by the interpolation section 25b based on the lattice point coordinate position information indicating the information of the coordinate positions of the lattice point for generating the pixel data of the raster scan system and the sampling coordinate position information of the detection signals around the coordinate position of the lattice point and that determines the number of detection signals to be used in the interpolation process by the interpolation section according to the specified sampling coordinate positions.

Figure 5A:
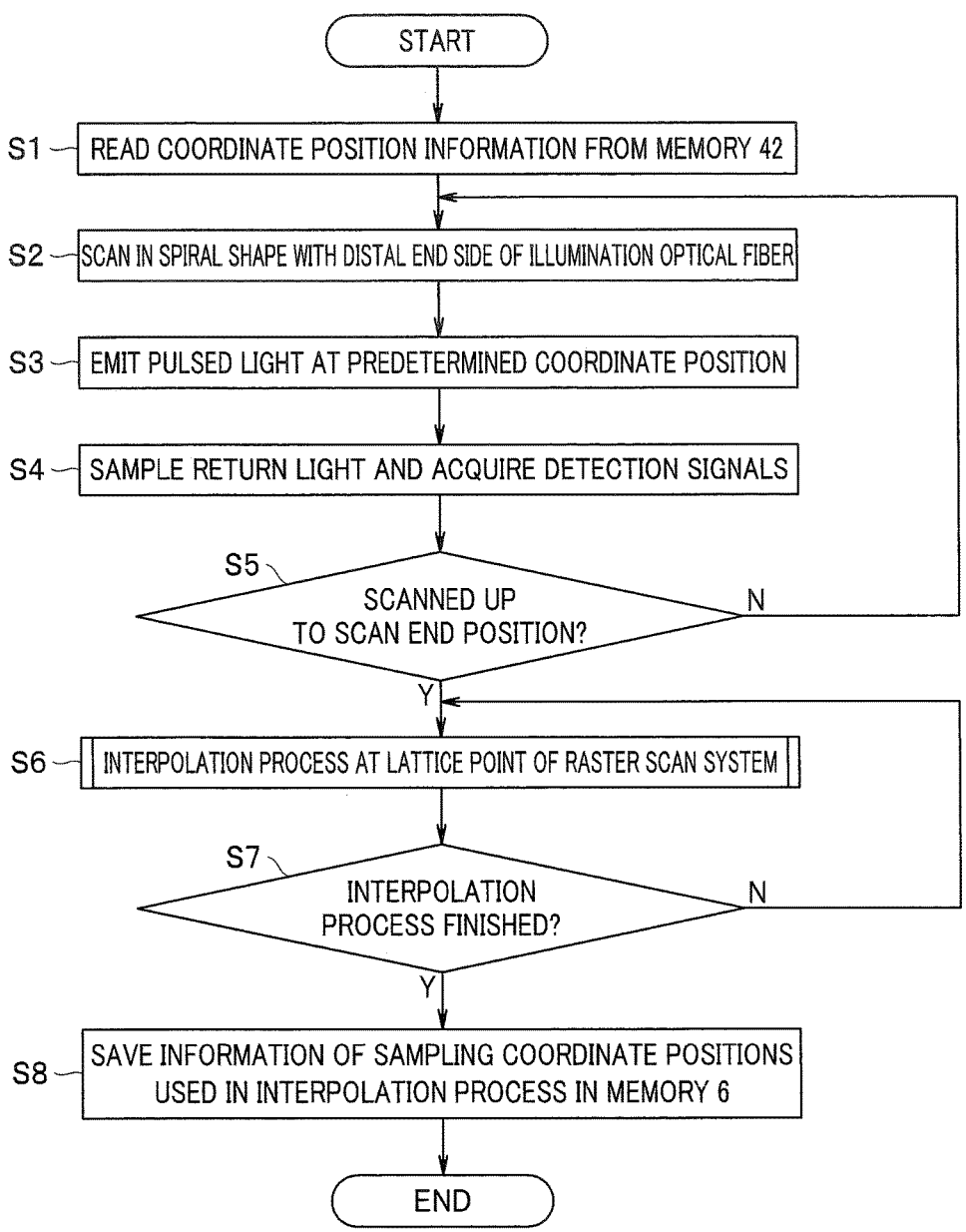
FIG. 5A is a flowchart showing a representative processing procedure of an interpolation process of the first embodiment.

Next, operation of the present embodiment will be described with reference to a flowchart of FIG. 5A. FIG. 5A shows a representative processing procedure including the interpolation process of the first embodiment.

In first step S1, the controller 25 reads the coordinate position information in the memory 42 and stores the coordinate position information in the memory 24. In next step S2, the controller 25 controls the drive unit 22 to apply the drive signals to the actuator section 16. As a result of the application of the drive signals, the actuator section 16 performs scanning (swinging) with the distal end side of the illumination optical fiber 13 in the spiral shape from the scan start position Pst shown in FIG. 3B.

In step S3, the light source light emission section 25a controls the light source unit 21 to discretely and sequentially emit pulsed light at the predetermined coordinate positions.

In step S4, the detection unit 23 acquires the detection signals by sequentially sampling the return light from the side of the subject 5 when the pulsed light is discretely emitted. The detection unit 23 stores the acquired detected signals in the memory of the interpolation section 25b or in the memory 24, for example.

In this case, a reference subject 5a made of a white plate or the like arranged in advance at a predetermined distance from the distal end surface of the insertion portion 11 may be used as the subject 5 (FIG. 1 shows the reference subject 5a by a dotted line). Note that the signals may be stored in the memory 24 instead of the memory of the interpolation section 25b.

In next step S5, the controller 25 judges whether the scanning is performed up to the scan end position Pen shown in FIG. 3B based on the drive signals. If the scanning has not reached the scan end position Pen, the controller 25 returns to the process of step S2 and continues the operation of applying the drive signals from the drive unit 22 to the actuator section 16. On the other hand, if the scanning has reached the scan end position Pen, the controller 25 applies the drive signals to the actuators to return from the scan end position to the scan start position Pst, and the interpolation section 25*b* executes the interpolation process at each lattice point of the raster scan system in this period as shown in step S6. Details of the interpolation process of step S6 will be described later with reference to FIG. 5B.

In step S7, the controller 25 judges whether the interpolation process is finished, and if the interpolation process is not finished, the controller 25 returns to the process of step S6 to continue the interpolation process of step S6.

On the other hand, if the interpolation process is finished, the controller 25 switches the selector switch 44 in step S8, and for example, the controller 25 stores (saves), in the memory 6, only the sampling coordinate position information used in the interpolation process in the sampling coordinate position information stored in the region information storage area 24*b* of the memory 24 and ends the interpolation process by the interpolation section 25.

The memory 6 saves only the sampling coordinate position information used in the interpolation process, and in a next time, the controller 25 uses the sampling coordinate position information stored (saved) in the memory 6 to cause the light source unit 21 to discretely emit pulsed light. In this case, the number of times of unnecessary pulsed light emission not used in the interpolation process can be reduced, compared to the state of the pulsed light emission before the interpolation process not used in the interpolation process. This can eliminate the unnecessary pulsed light emission by the light source unit 21, and lifetime of the laser light sources included in the light source unit 21 can be increased.

Figure 5B:
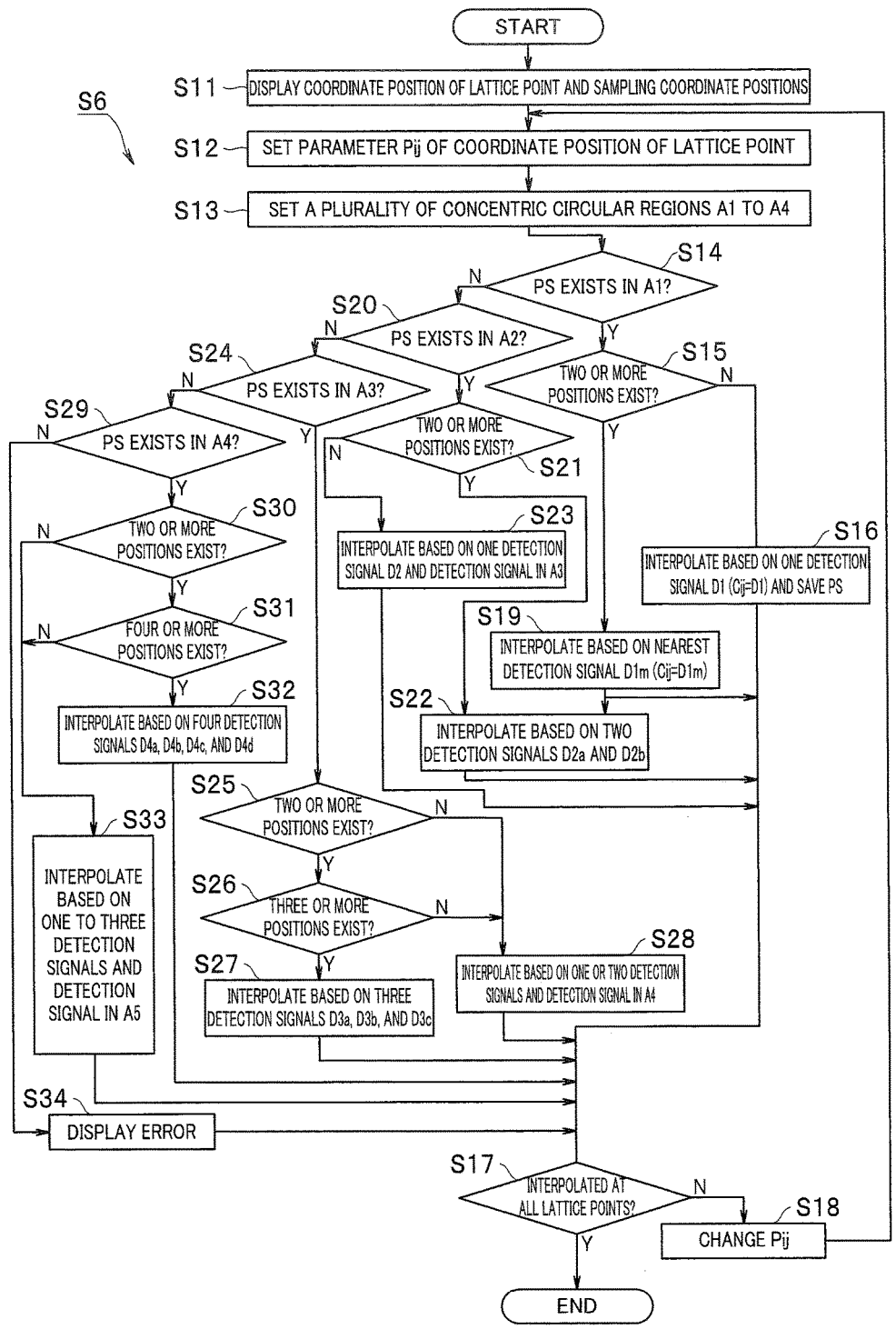
FIG. 5B is a flowchart showing an example of the processing procedure of the interpolation process in FIG. 5A.

FIG. 5B shows details of the interpolation process.

In first step S11, the interpolation section 25*b* displays the coordinate position of each lattice point and the sampling coordinate positions in a common coordinate system. The interpolation section 25*b* displays the coordinate positions (sampling coordinate positions) acquired from the memory 42 on a coordinate plane in which the coordinate position of each lattice point is displayed, for example.

In next step S12, the interpolation section 25*b* sets parameters (same Pij as the lattice points Pij is used for the simplification) indicating the coordinate positions of the lattice points Pij that are the coordinate positions of the pixel data to be generated. The parameters Pij are set to sequentially cover all lattice points included in a lattice point range R for generating the image of the raster scan system as shown on the left side of FIG. 4B, for example.

In FIG. 4B, i of the parameters Pij is sequentially increased by 1 from a left end to a right side of an uppermost first line. After the parameter Pij is set on a right end, j is increased by 1 to set j to 2, and the parameter i is sequentially increased by 1 from the left end to the right side in a second line. That is, i of the parameter Pij is a parameter indicating a lattice point position in a horizontal direction, and j is a parameter indicating a lattice point position in a vertical direction. An initial value of the parameter Pij is Pij=P11.

Figure 6A:
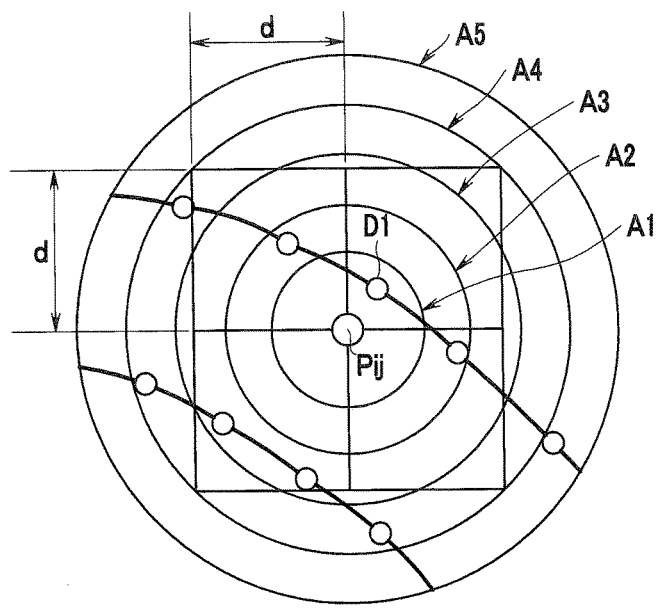
FIG. 6A is an explanatory diagram of the interpolation process, in which a lattice point is set as a reference position, a plurality of concentric circular regions are set according to distances from the lattice point, and a sampling coordinate position of a detection signal is detected within a nearest region (first region) at a closest distance from the lattice point among the plurality of regions.

In next step S13, the interpolation section 25*b* sets a plurality of concentric circular regions A1, A2, A3, ..., and An as shown in FIG. 6A based on the coordinate position of the lattice point Pij (the parameter Pij indicating the lattice point Pij). Note that although a case of the regions A1, A2, A3, A4, and A5 is illustrated in FIG. 6A, the case is not limited to the case of n=5, and n=4 or 3 or 2 may be set, or n=6 or more may be set. Although a case of a square lattice in which the distance between lattice points adjacent in the horizontal direction and the vertical direction is d in the lattice points Pij (the parameters Pij indicating the lattice points Pij) is described in FIG. 6A, a case in which the distance between lattice points in the horizontal direction and the distance between lattice points in the vertical direction are different can also be applied.

The first region A1 as an innermost region is, for example, a region in a circular shape with a radius of d/2 which is half the distance d between lattice points as shown in FIG. 5A. The second region A2 outside of the first region A1 is a region in a circular shape outside of the first region A1, with a radius of a value between d/2 and d.

The third region A3 outside of the second region A2 is a region in a circular shape with a radius of a value a little greater than d outside of the second region A2. The fourth region A4 outside of the third region A3 is, for example, a region in a circular shape with a radius of a value $2^{1/2} \times d$ that is a distance between lattice points in a diagonal direction outside of the third region A3. The fifth region A5 is set at substantially a same ring width (distance interval) as in the cases of A3, A4, and the like outside of the fourth region A4. Note that the values specifically setting or illustrating the regions A1 to A4, A5, and the like are examples, and the values are not limited to the values described above and the like. For example, a value smaller than d/2 may be set for the first region A1.

When the interpolation section 25*b* executes the interpolation process, the number-of-interpolations determination section 25*c* is set in advance to determine the number of detection signals to be used by the interpolation section 25*b* in the interpolation process according to the regions in which the detection signals are detected. As described below, the number-of-interpolations determination section 25*c* sets the number to 1 to 3 according to cases in which the detection signals exist in the first region A1 to the third region A3. The scanning pattern is usually set such that the detection signals exist before the third region A3. Although the case with the number set in this way is described, the number may be able to be changed to a different number.

According to the number determined by the number-of-interpolations determination section 25*c*, if the detection signal is detected in the first region A1, the interpolation section 25*b* generates image data Cij of the lattice point Pij (the parameter Pij indicating the lattice point Pij) based on one detection signal. If the detection signal is not detected in the first region A1, and the detection signal is detected in the second region A2, the interpolation section 25*b* generates the pixel data Cij of the lattice point Pij based on two detection signals.

If the detection signal is not detected in the first region A1 and the second region A2, and the detection signal is detected in the third region A3, the interpolation section 25*b* generates the pixel data Cij of the lattice point Pij based on three detection signals. Note that if the detection signal is not detected in the first region A1 to the third region A3, and the detection signal is detected in the fourth region A4, error processing is executed. However, the error processing may not be executed, and the pixel data Cij of the lattice point Pij may be generated based on four detection signals.

In next step S14, the interpolation section 25*b* judges whether a sampling coordinate position (abbreviated as PS) of the detection signal exists in the innermost first region A1. If the sampling coordinate position (abbreviated as PS) of the detection signal exists in the first region A1 as shown in FIG. 6A, the interpolation section 25*b* judges whether two or more sampling coordinate positions exist in next step S15.

If two or more sampling coordinate positions do not exist, (that is, if only a single sampling coordinate position exists as shown in FIG. 6A), the interpolation section 25*b* performs interpolation of setting a detection signal D1 of the sampling coordinate position existing in the first region A1 as the pixel data Cij of the lattice point Pij in next step S16 (Cij=D1). The sampling coordinate position used in the interpolation or information specifying the detection signal D1 is saved in the memory 24 or the like. Save PS is written in FIG. 5B.

After the process of step S16, the interpolation section 25b judges whether the interpolation is performed at all lattice points in step S17, and if the interpolation is performed at all lattice points, the interpolation section 25b ends the process of FIG. 5B. On the other hand, if the interpolation is not finished, the interpolation section 25b changes ij of the lattice point (parameter of the lattice point) Pij in step S18 and returns to the process of step S12. The interpolation section 25b continues the same process.

On the other hand, if a judgement result indicates that two or more sampling coordinate positions exist in step S15, the interpolation section 25b performs interpolation of setting a detection signal D1m of the sampling coordinate position closest to (that is, nearest to) the lattice point Pij as the image data Cij of the lattice point Pij in step S19 (Cij=D1m). In this case, the sampling coordinate position specifying the detection signal D1m is saved in the memory 24 or the like (saving is not illustrated in FIG. 5B).

If the judgement result of the interpolation section 25b in step S14 indicates that the sampling coordinate position of the detection signal does not exist in the first region A1, the interpolation section 25b judges whether the sampling coordinate position of the detection signal exists in the second region A2 in step S20.

Figure 6B:
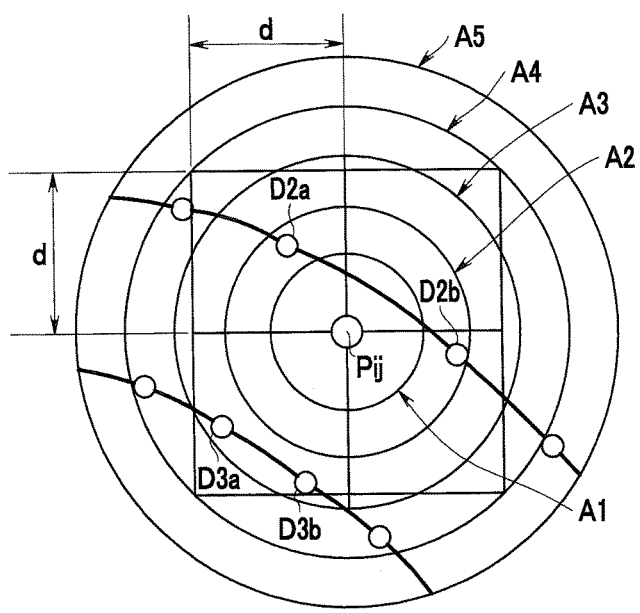
FIG. 6B is an explanatory diagram of the interpolation process, in which sampling coordinate positions of detection signals are detected within a second region outside of the nearest region.

FIG. 6B shows a situation of this case and shows an example in which the sampling coordinate position does not exist in the first region A1, and two detection signals D2a and D2b of the sampling coordinate positions exist in the second region A2. If the judgement result indicates that the sampling coordinate position of the detection signal exists in the second region A2 in step S20, the interpolation section 25b judges whether two or more sampling coordinate positions exist in next step S21.

If two or more sampling coordinate positions exist, the interpolation section 25b performs interpolation of setting the pixel data Cij of the lattice point Pij from the detection signals D2a and D2b of two sampling coordinate positions existing in the second region A2 in order of distance closest to the lattice point Pij in next step S22 (for example, Cij=(D2a+D2b)/2).

In this case, the sampling coordinate positions specifying the detection signals D2a and D2b are saved in the memory 24 or the like (not illustrated in FIG. 5B). The same process of saving is also executed in following steps S23, 27, 28, and the like.

Note that if two or more sampling coordinate positions do not exist in step S21, the interpolation section 25b uses a detection signal D2 of one sampling coordinate position existing in the second region A2 and a detection signal D3 of one sampling coordinate position existing in the third region A3 to perform interpolation of setting the pixel data Cij of the lattice point Pij in step S23. For example, the interpolation is performed by making a weight of the detection signal D2 in the second region A2 greater than a weight of the detection signal D3 in the third region A3 outside of the detection signal D2, such as Cij=(2×D2+D3)/3. If detection signals D1a and D3b of two sampling coordinate positions exist in the third region A3, the interpolation may be performed based on Cij=(2×D2+(D3a+D3b))/4.

If the judgement result indicates that the sampling coordinate position of the detection signal does not exist in the second region A2 in step S20, the interpolation section 25b judges whether the sampling coordinate position of the detection signal exists in the third region A3 in step S24.

If the judgement result indicates that the sampling coordinate position of the detection signal exists in the third region A3 in step S24, the interpolation section 25b judges whether two or more sampling coordinate positions exist in next step S25. If two or more sampling coordinate positions exist, the interpolation section 25b judges whether three or more sampling coordinate positions exist in next step S26. If three or more sampling coordinate positions exist in step S26, the interpolation section 25b performs interpolation of setting the pixel data Cij of the lattice point Pij by using detection signals D3a, D3b, and D3c of three sampling coordinate positions existing in the third region A3 in order of distance closest to the lattice point Pij in step S27 (for example, Cij=(D3a+D3b+D3c)/3). After the process of step S27, the process moves to step S17.

On the other hand, if two or more sampling coordinate positions do not exist in step S25, the interpolation section 25b in step S28 uses one detection signal D3 in the interpolation of the detection signal in step S23. If two or more sampling coordinate positions exist, and three or more sampling coordinate positions do not exist in step S26, the interpolation section 25b in step S28 uses two detection signals D3a and D3b in the interpolation of the detection signal D2 of step S23. After the process of step S28, the process moves to step S17.

If the judgement result indicates that the sampling coordinate position of the detection signal does not exist in the third region A3 in step S24, the interpolation section 25b judges whether the sampling coordinate position of the detection signal exists in the fourth region A4 in step S29. If the judgement result indicates that the sampling coordinate position of the detection signal exists in the fourth region A4, the interpolation section 25b judges whether two or more sampling coordinate positions exist in step S30. If two or more sampling coordinate positions exist, the interpolation section 25b judges whether four or more sampling coordinate positions exist in next step S31. If four or more sampling coordinate positions exist in step S31, the interpolation section 25b performs interpolation of setting the pixel data Cij of the lattice point Pij by using detection signals D4a, D4b, D4c, and D4d of four sampling coordinate positions existing in the fourth region A4 in order of distance closest to the lattice point Pij in step S32 (for example, Cij=(D4a+D4b+D4c+D4d)/4). After the process of step S32, the process moves to step S17.

On the other hand, if two or more sampling coordinate positions do not exist in steps S30 and S31, the interpolation section 25b performs interpolation by using one to three detection signals and the detection signal in the fifth region A5 (see FIG. 6A) outside of the fourth region A4 in step S33.

If the sampling coordinate position of the detection signal does not exist in the fourth region A4 in step S29, the interpolation section 25b displays an error in step S34 because such a case usually does not occur. After the process of step S33 or S34, the process moves to step S17.

As a result of the process shown in FIG. 5B, the pixel data arranged on each lattice point (of the raster scan system) can be generated in a normal operation state, and the image I2 of the raster scan system with good image quality can be generated.

Therefore, the present embodiment can provide the scanning endoscope apparatus 1 that can generate the image I2 of the raster scan system with good image quality by executing the interpolation process even if the detection signal does not exist near the lattice point of the raster scan system.

According to the present embodiment, the detection signal existing at a distance closest from each lattice point is prioritized to generate the pixel data for forming the image of the raster scan system, and an image of the raster scan system with good image quality can be generated.

According to the present embodiment, the light source is controlled to emit light only at the coordinate positions used in the interpolation process saved in advance. Therefore, compared to when the information of the coordinate positions not used in the interpolation process is also saved, the memory capacity of the memory 6 provided on the scanning endoscope 2 can be reduced. The number of times of unnecessary light emission of the light source can be reduced, and the lifetime of the light source can be increased. Furthermore, power can also be saved.

In the interpolation process described in FIG. 5B, a plurality of detection signals are used to execute the interpolation process in the regions Ak (k=2, 3, 4) other than the first region A1 outside of the first region A1. In this case, a plurality of detection signals may be used to execute the interpolation process as described below.

Figure 7:
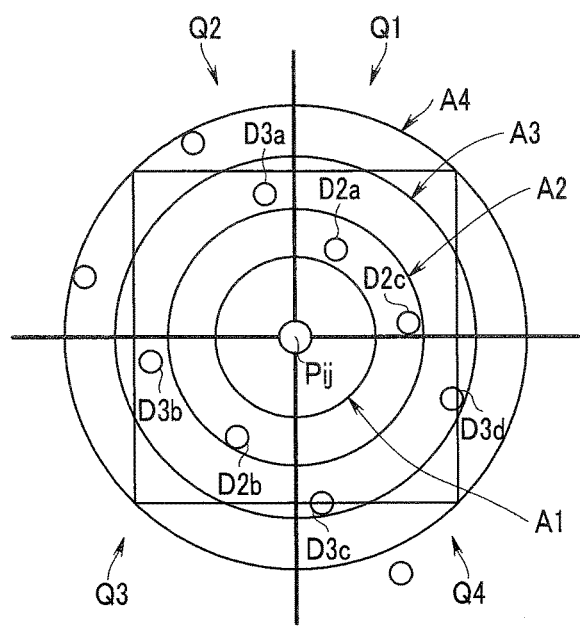
FIG. 7 is an explanatory diagram of a case in which detection signals of different quadrants are used to execute the interpolation process.

FIG. 7 shows an explanatory diagram of this case. For example, when the interpolation process is to be executed by a plurality of detection signals in the second region A2, first to fourth quadrants Q1 to Q4 around the lattice point Pij are set as shown in FIG. 7. For example, when the detection signal D2a of the nearest sampling coordinate position exists, the detection signal D2a and the detection signal D2b of the sampling coordinate position existing in a quadrant other than the quadrant (first quadrant in FIG. 7) with the detection signal D2a are used to execute the interpolation process. Although a detection signal D2c further exists in the first quadrant Q1 in the example of FIG. 7, the detection signal D2c is not used. Although the area is evenly divided into four quadrants in the specific example described in FIG. 7, the area may be divided into two equal parts (for example, dividing the area into two equal parts in an up-down direction or a left-right direction), or the area may be divided into eight equal parts. The number of evenly divided regions is not limited.

Although the case of the second region A2 is described in the specific example, one detection signal from each of different quadrants is used to execute the interpolation process when three detection signals D3a, D3b, and D3c are to be used to execute the interpolation process in the third region A3, for example. Two detection signals D3c and D3d exist in the fourth quadrant Q4 in FIG. 7. For example, one detection signal D3c is used in the interpolation process, and the other detection signal D3d is not used in the interpolation process.

In this way, the detection signals existing in different quadrants can be preferentially used to execute the interpolation process. As a result, deviation of the detection signals used in the interpolation process can be reduced, and an image with good image quality can be generated.

In the description above, a plurality of detection signals are used to execute the interpolation process in the regions Ak other than the first region A1 outside of the first region A1. In the example described above, the detection signals of the fourth region A4 outside of the third region A3 are used to execute the interpolation process in the third region A3 if three detection signals do not exist in the third region A3, for example.

In such a case, a search range of the detection signals used in the interpolation process may be limited. For example, in the interpolation process, a limitation may be set to execute the interpolation process by using the detection signals existing within the third region A3 from the lattice point. For example, in step S28 of FIG. 5B, the number of sampling coordinates may be reduced to execute the interpolation process based on one or two detection signals in the third region A3. Alternatively, the number of sampling coordinates may be reduced to execute the interpolation process based on the detection signals within the fourth region A4 in the process of step S31.

When the interpolation section 25b executes the interpolation process of using two or more detection signals specified according to the distance from the lattice point Pij to generate the pixel data of the raster scan system, the interpolation section 25b may place a larger weight on a detection signal with a smaller distance from the lattice point Pij to generate the pixel data. The distance in this case may not be one value, and the value may be changed in a plurality of distance ranges to place a larger weight on a detection signal belonging to (existing in) a distance range with a smaller distance from the lattice point Pij to generate the pixel data.

Although the generation of the pixel data of the lattice points included in the rectangular lattice point range R is described as shown in FIG. 4B, the lattice points, such as a lattice point P11, are at positions out of the scanning pattern (scanning trajectory) in a spiral pattern. Therefore, a plurality of detection signals away from the lattice points need to be used to execute the interpolation process, and reliability is lower than pixel data in a case of lattice points at a distance closer to the scanning pattern (scanning trajectory).

Figure 8:
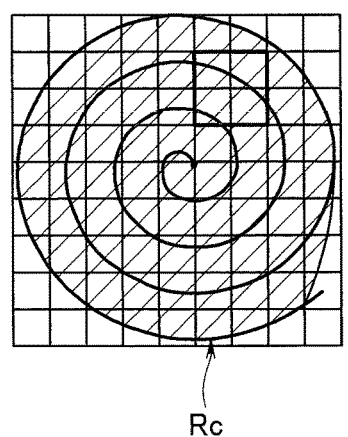
FIG. 8 is an explanatory diagram of a case with a limitation to a range Rc close to a region of a scanning pattern (scanning trajectory) in a spiral shape in generating an image of a raster scan system.

Therefore, the range of the lattice points in generating the image of the raster scan system may be limited according to the scanning pattern (scanning trajectory) in the spiral shape. For example, according to a scanning pattern (scanning trajectory) in a spiral shape of FIG. 8, the image I2 of the raster scan system may be generated in a range Rc indicated by oblique lines close to the region of the scanning pattern (scanning trajectory) in the spiral shape. At a lattice point outside of an outermost circular pattern, the interpolation section 25b may not generate the pixel data of the lattice point.

Figure 9:
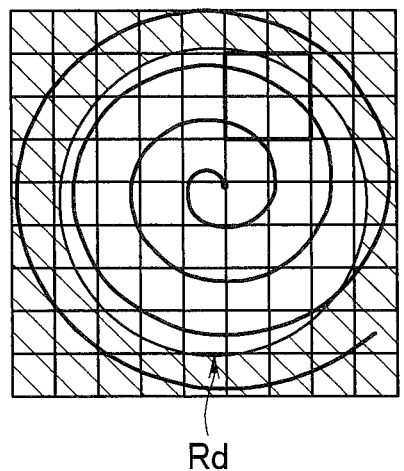
FIG. 9 is an explanatory diagram of a case in which a scanning pattern on an outermost periphery side is masked and not displayed after scanning in a spiral shape.

After swinging in the spiral shape, deviation of the scanning position on the outermost periphery side from a predetermined position may be large when there are individual differences (or variations) in the actuator section 16 provided on the scanning endoscope 2 or when conditions of a use environment (surrounding temperature) are different. Therefore, as shown for example in FIG. 9, the scanning pattern on the outermost periphery side may be masked as indicated by oblique lines, and only a region Rd not masked inside of the outermost periphery side may be used to display the scan range, the image, and the like.

In the interpolation by the interpolation section 25b described above, the number of detection signals to be used in the interpolation is mainly determined according to the size of the distance from a center position based on the lattice point Pij to the sampling coordinate position where the detection signal exists.

A movement speed in moving the distal end of the illumination optical fiber 13 to form the trajectory of the spiral shape may be different between a center side of the trajectory in the spiral shape and a periphery side out of the center, and intervals (pitches) between spirals adjacent in a distance direction from the center may also be different between the center side and the periphery side. To facilitate handling such a case, the number of detection signals to be used in the interpolation process may be determined according to the sampling coordinate position and the distance from the center of the trajectory in the spiral shape.

For example, an input section 40 including a keyboard or the like may be provided as indicated by a dotted line in FIG. 1. Number determination information for determining the number of detection signals to be used in the interpolation process may be inputted to the controller 25 (the number-of-interpolations determination section 25c of the controller 25) from the input section 40, and the controller 25 (the number-of-interpolations determination section 25c of the controller 25) may determine the number of detection signals according to the number determination information.

For example, the plurality of regions A1, A2, A3, and the like are set around the lattice point Pij according to the distance from the lattice point Pij in FIG. 6A. However, a plurality of concentric circle regions (will be called E1, E2, E3, and the like) may be further set as in the case of the plurality of regions A1, A2, and the like around the center (that is, the scan start position Pst) of the trajectory in the spiral shape according to the distance from the center, and the number of detection signals to be used in the interpolation process may be increased as the region separates from the center (in other words, with an increase in the distance from the center).

For example, three detection signals of the third region A3 are used to perform the interpolation in step S27 of FIG. 5B in the description of the first embodiment. However, the number may be maintained in the region E1 in which the lattice point Pij in this state is close to the center, and the number of detection signals to be used in the interpolation process may be increased in the region E3 (or E2) farther from the center than in the case of the region E1 so as to perform the interpolation by using four detection signals, for example. This may be applied to the regions other than the third region A3.

The number of detection signals to be used in the interpolation may be reduced with an increase in the number of lines of the trajectory in the spiral shape in the distance direction from the center of the trajectory in the spiral shape.

Figure 10:
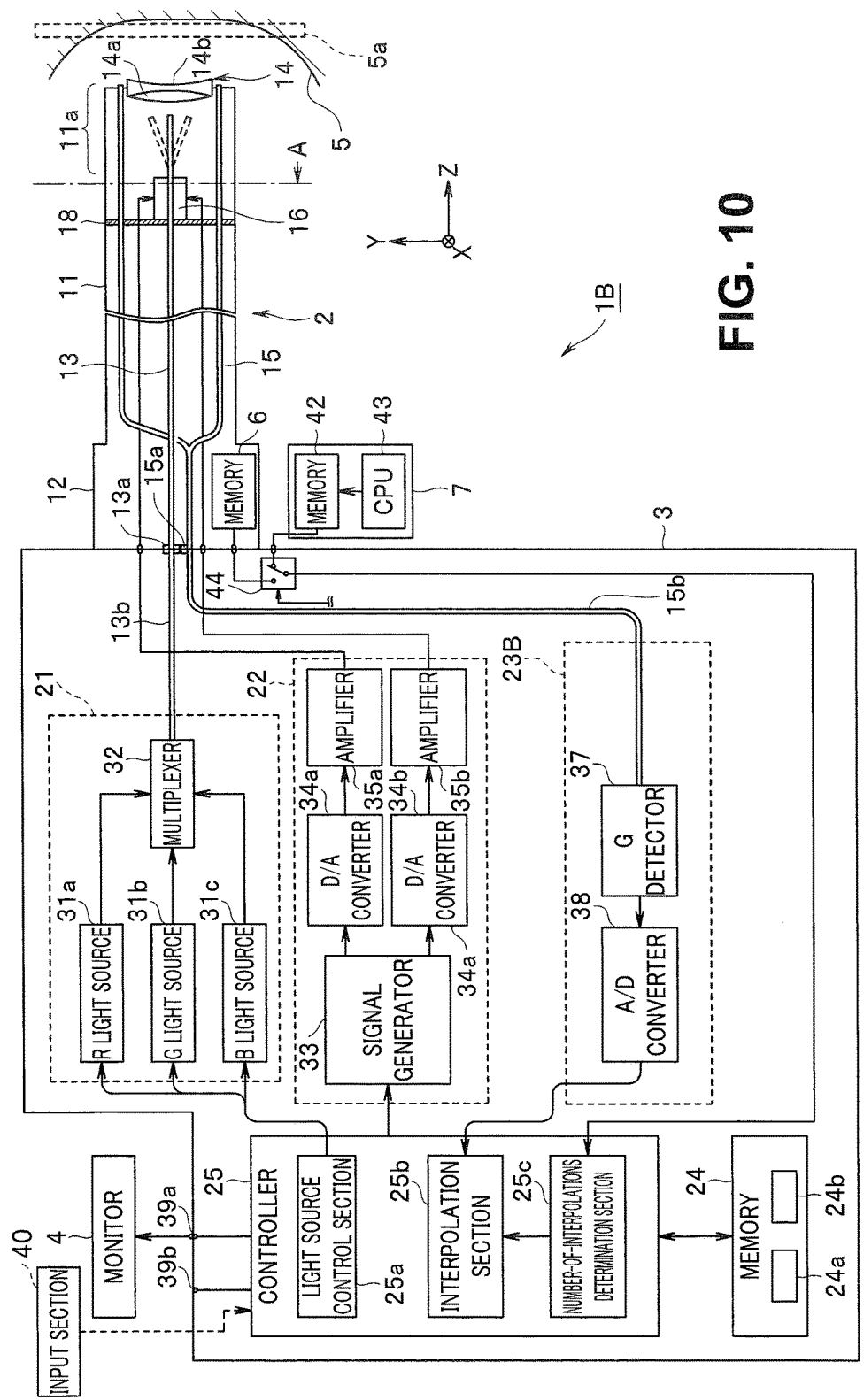
FIG. 10 is a diagram showing an entire configuration of a scanning endoscope apparatus according to a modification of the first embodiment.

Although the case of the scanning endoscope apparatus 1 that simultaneously emits the illuminating light of the R light, the G light, and the B light is described in the embodiment, the same can be applied to a case of a scanning endoscope apparatus of a time-division multiplex system (TDM) that temporally shifts and sequentially emits the illuminating light of the R light, the G light, and the B light as in the scanning endoscope apparatus 1B of a modification shown in FIG. 10.

The light source control section 25a controls the R light source 31a, the G light source 31b, and the B light source 31c in the light source unit 21 to temporally shift and sequentially emit light, and the sequentially emitted R, G, and B light is guided to the distal end side of the illumination optical fiber 13 through the multiplexer 32 and emitted toward the subject 5.

The return light of the emitted illuminating light of the R light, the G light, and the B light sequentially emitted toward the subject 5 is received by the distal end of the light receiving optical fiber 15 and guided to the proximal end side of the light receiving optical fiber 15. In a detection unit 23B shown in FIG. 10, the demultiplexer 36 of FIG. 1 is not necessary. One detector 37 performs photoelectrical conversion, and one A/D converter 38 performs A/D conversion of the photoelectrically converted signal. The detection signal after the A/D conversion is saved as pixel data of R, G, and B in the memory in the controller 25 or in the memory 24.

The other components are the same as the components in the case of the scanning endoscope apparatus 1 shown in FIG. 1.

Action of the present modification is substantially the same action if the action in the case of emitting and receiving the white color light in FIG. 1 is changed to the case of emitting and receiving the R light, the G light, and the B light.

Therefore, effects of the present modification are also substantially the same as in the case of the first embodiment.

However, an amount of information of the coordinate positions stored in the memory 6 in the scanning endoscope 2 is three times the amount of information of the coordinate positions, in order to maintain a same level of resolution as in the first embodiment.

Note that the memory capacity for saving in the memory 6 needs to be large. When the interpolation section 25b executes the interpolation process, the information specifying the detection signals Di to be used in the interpolation process at each lattice point Pij and the information of the number of the detection signals Di may be saved in advance in the memory 6 to allow reducing the process of searching the presence or absence of the sampling coordinate positions of the detection signals D in the plurality of regions A1, A2, and the like shown in FIG. 6. The user or the like may be able to change and set the range of the plurality of regions A1, A2, A3, and the like from the input section 40 according to the distance from the lattice point Pij, the distance d between lattice points, and the like. The user or the like may be able to change and set the number of detection signals to be used in the interpolation process set corresponding to the regions set according to the distance from the lattice point Pij.

What is claimed is:
1. An image processing apparatus comprising:
a processor comprising hardware, wherein the processor is configured to:
in a first time, receive detection signals from a detector of a scanning endoscope sequentially sampling return light from a subject scanned with pulsed illuminating light emitted by a light source of the scanning endoscope;
perform a determination process to determine a number of the detection signals that can be used in an interpolation process based on distances between a coordinate position of a predetermined lattice point in pixel data of a raster scan system and sampling coordinate positions of the detection signals around the coordinate position of the predetermined lattice point; and
perform the interpolation process to generate pixel data of the predetermined lattice point, wherein the interpolation process is performed based on one or more of the detection signals wherein a number of the detection signals used in the interpolation process is limited by the number of the detection signals that can be used determined in the determination process; and
in a second time subsequent to the first time, control positions where the light source emits pulsed illumination light based on sampling coordinate positions of the detection signals used in the interpolation process.

2. The image processing apparatus according to claim 1, wherein the processor is configured to increase the number of the detection signals that can be used in the interpolation process with an increase in the distance between the coordinate position of the predetermined lattice point and a sampling coordinate position of a detection signal nearest to the coordinate position of the predetermined lattice point among the detection signals.

3. The image processing apparatus according to claim 2, wherein when one or more of the sampling coordinate positions of the detection signals that can be used in the interpolation process is positioned within a set distance from the coordinate position of the predetermined lattice point, wherein the set distance is set to about ½ of a distance between the predetermined lattice point and an adjacent lattice point in the pixel data of the raster scan system, the processor is configured to:
   determine, in the determination process, that the number of the detection signals that can be used in the interpolation process is one; and
   generate, in the interpolation process, the pixel data of the predetermined lattice point based on one detection signal with a sampling coordinate position nearest to the coordinate position of the predetermined lattice point.

4. The image processing apparatus according to claim 2, wherein when the processor performs the interpolation process to generate the pixel data of the predetermined lattice point based on two or more detection signals specified according to the distances from the predetermined lattice point, the processor is configured to place a larger weight on a detection signal of the two or more detection signals with a smaller distance from the predetermined lattice point to generate the pixel data.

5. The image processing apparatus according to claim 2, wherein the processor is configured to:
   control a memory to save in advance, as first sampling coordinate position information, information of the sampling coordinate positions of the detection signals received from the detector used in the determination process to determine the number of the detection signals that can be used in the interpolation process; and
   extract, from the first sampling coordinate position information, only second sampling coordinate position information as information of the sampling coordinate positions of the detection signals used in the interpolation process; and
   in the second time, control the positions where the light source emits pulsed illumination light based on the second sampling coordinate position information.

6. The image processing apparatus according to claim 1, wherein when the processor determines, in the determination process, that the number of the detection signals that can be used in the interpolation process is two or more,
   the processor is configured to:
   divide a region around the predetermined lattice point into a plurality of regions; and
   wherein when a first detection signal and a second detection signal exists in one region of the plurality of regions, and the processor, in the interpolation process, generates the pixel data of the predetermined lattice point based on at least the first detection signal, the processor is further configured to prioritize using a third detection signal existing in another region of the plurality of regions in performing the interpolation process over the second detection signal in the one region to perform the interpolation process.

\* \* \* \* \*